US012122699B2

(12) United States Patent
Zhou et al.

(10) Patent No.: US 12,122,699 B2
(45) Date of Patent: Oct. 22, 2024

(54) METHOD FOR CONSTRUCTING HALOPHILIC NITROGEN ASSIMILATION MICROBIOME

(71) Applicant: SHANDONG UNIVERSITY, Shandong (CN)

(72) Inventors: Weizhi Zhou, Jinan (CN); Mengru Zhang, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 412 days.

(21) Appl. No.: 17/590,475

(22) Filed: Feb. 1, 2022

(65) Prior Publication Data

US 2022/0242765 A1 Aug. 4, 2022

(30) Foreign Application Priority Data

Feb. 1, 2021 (CN) ......................... 202110137887.9
Jul. 26, 2021 (CN) ......................... 202110844368.6

(51) Int. Cl.
*C02F 3/34* (2023.01)
*C02F 3/12* (2023.01)
*C12N 1/20* (2006.01)

(52) U.S. Cl.
CPC .............. *C02F 3/34* (2013.01); *C02F 3/1263* (2013.01); *C12N 1/205* (2021.05)

(58) Field of Classification Search
CPC ...... C02F 3/34; C02F 3/1263; C02F 2101/16; C02F 2103/005; C02F 2103/08;
(Continued)

(56) References Cited

U.S. PATENT DOCUMENTS

2009/0145844 A1* 6/2009 Chang ..................... C02F 3/121 210/903
2019/0055584 A1* 2/2019 Reverso .................. C12P 39/00
2019/0071335 A1* 3/2019 Zhou ......................... C12P 3/00

FOREIGN PATENT DOCUMENTS

CN 105754904 A * 7/2016 ................ C02F 3/34
CN 107626285 A * 1/2018
(Continued)

OTHER PUBLICATIONS

English Translation of publication CN-105754904-A, Jul. 13, 2016. (Year: 2016).*
(Continued)

*Primary Examiner* — Joseph W Drodge
(74) *Attorney, Agent, or Firm* — Oliff PLC

(57) ABSTRACT

The present invention provides a method for constructing a halophilic nitrogen assimilation microbiome, and belongs to the technical fields of microorganisms as well as environmental governance and restoration. According to the present invention, a strain of *Psychrobacter aquimaris* A4N01 is screened from marine sediments; the strain can assimilate ammonia nitrogen to synthesize organic nitrogen, and simultaneously convert organic matters and phosphorus. A halophilic nitrogen assimilation microbiome developed by the strain has good nutrient conversion removal capacity and settling performance, has wide tolerance to salinity, and can be used in high-salinity wastewater treatment, saline-alkali soil fertilization, etc., so as to realize recycling of nutrient elements such as nitrogen and phosphorus in high-salinity environments. The method is simple in operation and low in costs and is environmentally friendly, therefore having good practical application value.

5 Claims, 5 Drawing Sheets

(58) Field of Classification Search
CPC ........... C02F 3/341; C12N 1/205; C12N 1/20; C12N 1/36; C12R 2001/01
See application file for complete search history.

(56) References Cited

FOREIGN PATENT DOCUMENTS

| | | | | | |
|---|---|---|---|---|---|
| CN | 107739086 | A | | 2/2018 | |
| CN | 109626599 | A | * | 4/2019 | .............. C02F 3/341 |
| WO | WO-2017177773 | A1 | * | 10/2017 | ................ C02F 3/02 |

OTHER PUBLICATIONS

Publication by Sunipaw Chankaew et al., "Nitrogen Removal Efficiency of Salt-tolerant Heterotrophic Nitrifying Bacteria", Published in Chiang Mai J. Sci., 2017, vol. 44(x), pp. 1-10. (Year: 2017).*
English Translation of publication CN-107626285-A, Jan. 26, 2018. (Year: 2018).*
English Translation of publication CN-109626599-A, Apr. 16, 2019. (Year: 2019).*
English translation of Huang publication WO-2017177773-A1, published Oct. 19, 2017. (Year: 2017).*

* cited by examiner

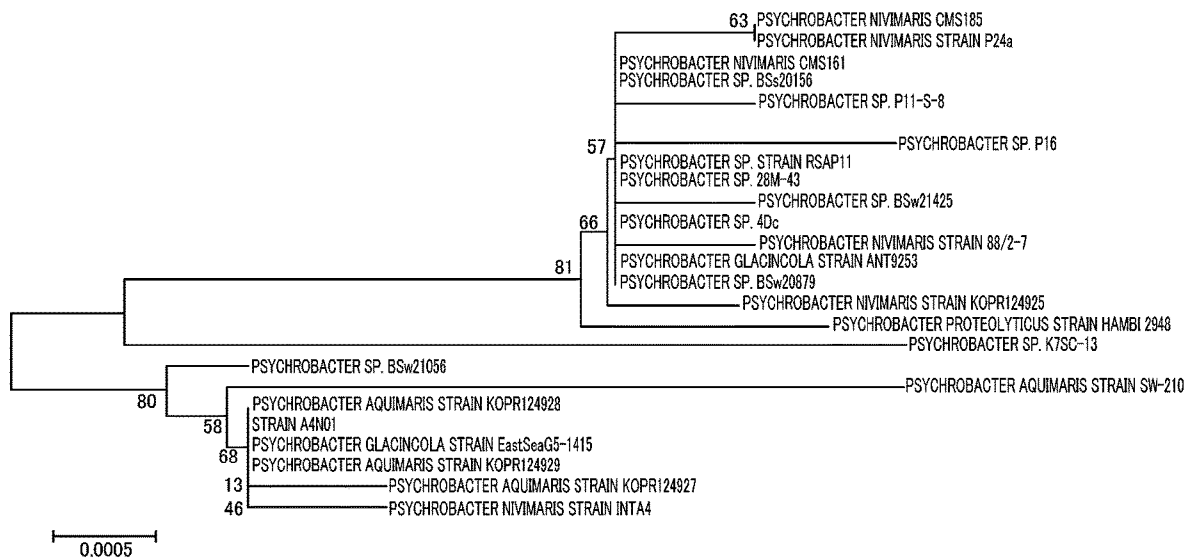
FIG. 1
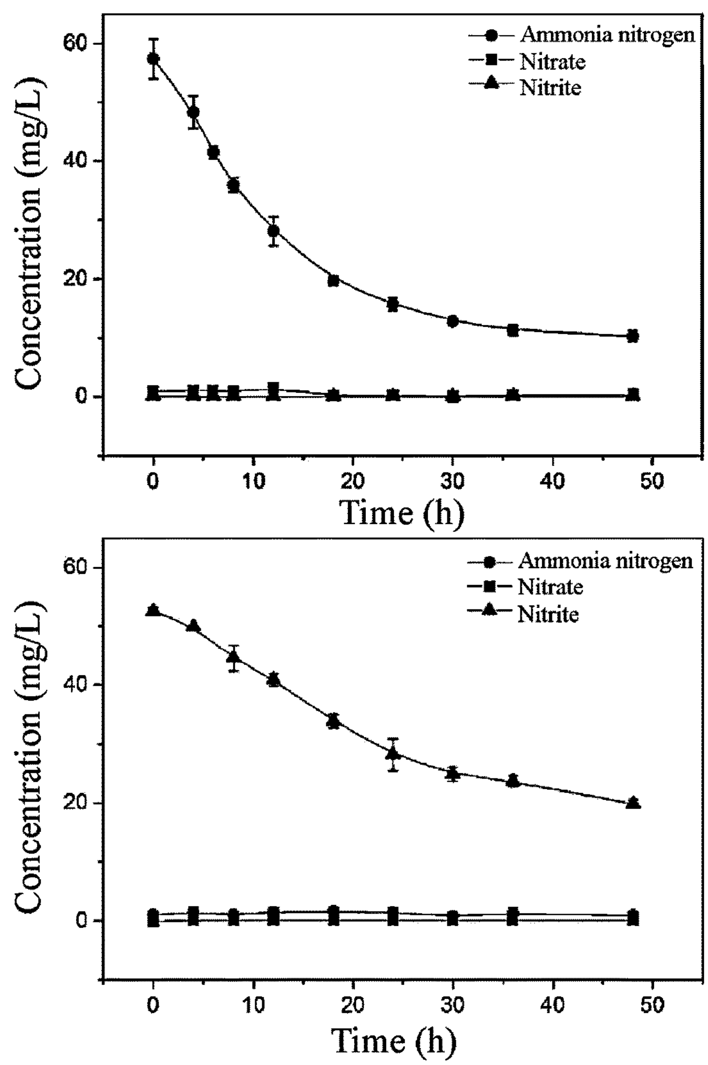

METHOD FOR CONSTRUCTING HALOPHILIC NITROGEN ASSIMILATION MICROBIOME

TECHNICAL FIELD

The present invention belongs to the technical fields of microorganisms as well as environmental governance and restoration, and particularly relates to a method for constructing a halophilic nitrogen assimilation microbiome.

BACKGROUND

The information disclosed in this Background section is only intended to enhance the understanding to the general background of the present invention and should not necessarily be taken as an acknowledgement or any form of implication that this information forms the prior art already known to a person of ordinary skill in the art.

Salt stresses inhibit the nutrient bioconversion in high-salinity environments, resulting in great challenges in high-salinity wastewater treatment, difficulties in nutrients circulation in saline-alkali soil, which leads to a large amount of nutrients entering environmental water bodies with salts, posing a great risk to the ecological safety. Therefore, it is necessary to establish an efficient halophilic nutrient conversion technology and method. Treatment methods for wastewater are mainly biological methods which convert nutrients through microbial metabolic activities, especially driven by nitrogen metabolism. Substance conversion in the high-salinity environments also need rely on the action of microorganisms. The nitrogen is removed mainly by nitrification-denitrification of the microorganisms, including the following steps: oxidizing, by ammonia oxidizing bacteria, ammonia nitrogen in the sewage into nitrite, oxidizing, by nitrite oxidizing bacteria, the nitrite into nitrate, and then reducing, by denitrifying bacteria, the nitrate to nitrite, thus converting into nitrogen gas. However, in this process, the nitrite oxidizing bacteria which are very sensitive to the salinity are inhibited by the salinity, thus the nitrification-denitrification pathway is inhibited and the nitrite accumulates, resulting in a decrease in the nitrogen removal efficiency. Meanwhile, the conversion of nitrogen into nitrogen gas which is difficult to utilize leads to the loss of nitrogen in the ecosystem and is also accompanied with generation of greenhouse gases such as nitrous oxide. In addition, in the high-salinity environments, the removal of organic matters and phosphorus is also inhibited, making it difficult to simultaneously remove pollutants in the high-salinity wastewater.

The key to nutrient bioconversion by a biological method is to find a salt-tolerant strain which can utilize pollutants such as organic matters, nitrogen, and phosphorus and be stable in an environmental microbiome. Chinese patent CN107739086A disclosed a method for removing nitrogen from high-salinity wastewater by utilizing sludge developed from marine sediments or mud. By gradually reducing the carbon-nitrogen ratio and increasing the concentrations of ammonia nitrogen and total nitrogen, each process realizes stable operation after about 30 days and then enters the next step, and the sludge is domesticated after 59 days. When the sludge was used to treat wastewater with the chloride ion concentration of 10-30 g/L, 95% of nitrogen of the total nitrogen removal rate was removed by assimilation, and the total nitrogen removal rate reached 90%. However, the inventors have found that due to the diversity of microbial communities, the metabolic characteristics of the sludge used in the method are unclear, resulting in complicated regulating methods, long sludge domestication time, slow system startup, etc. At the same time, this makes it impossible to realize directional construction and regulation in complex high-salinity wastewater environment.

SUMMARY

In view of the above deficiencies in the prior art, the present invention provides a method for constructing a halophilic nitrogen assimilation microbiome. According to the present invention, a strain of *Psychrobacter aquimaris* is screened from marine sediments. The strain assimilates ammonia nitrogen to synthesize organic nitrogen, and simultaneously converts organic matters and phosphorus. Meanwhile, studies unexpectedly find that the halophilic nitrogen assimilation microbiome developed by the strain also has good nutrient conversion removal capacity and settling performance, has wide tolerance to salinity, and can be used in high-salinity wastewater treatment, saline-alkali soil fertilization, etc., so as to realize recycling of nutrient elements such as nitrogen and phosphorus in the high-salinity environments. The method is simple in operation and low in costs and is environmentally friendly, therefore having good practical application value.

In order to realize the above technical purpose, the present invention adopts the following technical schemes.

In a first aspect of the present invention, a strain of *Psychrobacter aquimaris* A4N01 is provided. The strain has been deposited in China Center for Type Culture Collection (address: Wuhan University, Luojiashan, Wuchang, Wuhan City, Hubei Province) on Jan. 20, 2021 with a biological deposit number of CCTCC NO: M 2021120.

In a second aspect of the present invention, a microbial agent is provided, and the microbial agent contains the above *Psychrobacter aquimaris* A4N01.

In a third aspect of the present invention, a halophilic nitrogen assimilation microbiome is provided, which contains the above *Psychrobacter aquimaris* A4N01. More specifically, the halophilic nitrogen assimilation microbiome is obtained by inoculating the above *Psychrobacter aquimaris* A4N01 into high-salinity wastewater for culturing. Specifically, the halophilic nitrogen assimilation microbiome may be high-salinity wastewater obtained by the above treatment or activated sludge obtained by the above treatment.

In a fourth aspect of the present invention, a method for constructing the above halophilic nitrogen assimilation microbiome is provided, which includes:

inoculating the above *Psychrobacter aquimaris* A4N01 into a bioreactor containing high-salinity wastewater, and operating until stable ammonia nitrogen removal efficiency and settling performance are realized, to obtain a halophilic nitrogen assimilation microbiome.

In a fifth aspect of the present invention, application of the above *Psychrobacter aquimaris* A4N01, the microbial agent and/or the halophilic nitrogen assimilation microbiome in any one or more of the following is provided:

a) single-cell protein synthesis;
b) recycling of nitrogen and phosphorus nutrients;
c) wastewater treatment;
d) preparation of organic fertilizer;
e) improvement of soil fertility;
f) saline-alkali soil bioremediation;
g) governance of eutrophic water body;
h) pollution restoration of water body; and
i) greenhouse gas reduction and carbon neutral.

In b), nitrogen is metabolized based on assimilation.

In c), the wastewater includes high-salinity wastewater, aquaculture wastewater, industrial saline wastewater and seawater toilet-flushing wastewater.

In g), the water body includes freshwater and seawater, and seawater is preferred.

In a sixth aspect of the present invention, a method for nutrient integration and resource conversion in a high-salinity environment is provided. The method includes applying the above *Psychrobacter aquimaris* A4N01, the microbial agent and/or the halophilic nitrogen assimilation microbiome to the high-salinity environment.

More specifically, the high-salinity environment is a high-salinity water environment, and the high-salinity water environment has a salinity of not less than 2% (w/w), further preferably of 3%-7% (w/w).

The one or more technical schemes described above have the following beneficial technical effects:

1. In the above technical schemes, the strain of *Psychrobacter aquimaris* A4N01 with functions of flocculation and nitrogen assimilation is obtained through screening and separation. Studies have found that the strain can metabolize ammonia nitrogen through assimilation without generating nitrate and nitrite, does not produce nitrogen loss, has a wide salinity tolerance range, and can realize integrated removal of nutrients such as carbon, nitrogen, and phosphorus. The strain can promote the formation of the halophilic nitrogen assimilation microbiome, and by managing a structure of the microbiome, a metabolic direction of the microbiome developed by the strain can be regulated.

2. In the method for developing the halophilic nitrogen assimilation microbiome by nitrogen assimilation marine self-flocculating bacteria in the above technical schemes, initiation and culture of the microbiome are carried out in simulated wastewater with a salinity of 3% without salinity gradient domestication. The method is rapid in initiation, short in time consumption, simple in operation and low in cost.

3. In the above technical schemes, the halophilic nitrogen assimilation microbiome removes ammonia nitrogen through assimilation. When the halophilic nitrogen assimilation microbiome is used for treating high-salinity wastewater, no nitrite or nitrate is generated, the ammonia nitrogen and total nitrogen removal efficiency is high, and nitrogen loss is avoided, which indicate that the halophilic nitrogen assimilation microbiome has the advantage of greenness and high efficiency, and a new way of biologically removing nitrogen from high-salinity wastewater is provided.

4. The halophilic nitrogen assimilation microbiome in the above technical schemes has good organic matter and phosphorus removal capacity and good settling performance, and can realize recycling of nutrients in the high-salinity wastewater. The halophilic nitrogen assimilation microbiome contains a large amount of organic matters and organic nitrogen, so that can be used for organic fertilizer preparation, and has wide application prospects in the fields of biological improvement of soil, fertility immobilization of saline-alkali soil and the like.

5. The halophilic nitrogen assimilation microbiome in the above technical schemes has certain removal efficiency on ammonia nitrogen in the high-salinity wastewater with a salinity of 3%-7% (w/w), has high impact tolerance to different salinities, can be applied to treatment of high-salinity wastewater such as aquaculture wastewater, industrial saline wastewater and seawater toilet-flushing wastewater, so that its application in wastewater treatment systems has wide industrial application prospects.

BRIEF DESCRIPTION OF THE DRAWINGS

The accompanying drawings constituting a part of the present invention are used to provide a further understanding of the present invention. The exemplary embodiments of the present invention and descriptions thereof are used to explain the present invention, and do not constitute an improper limitation of the present invention.

FIG. 1 shows a phylogenetic tree of *Psychrobacter aquimaris* A4N01 according to the present invention.

DETAILED DESCRIPTION

Figure 2:
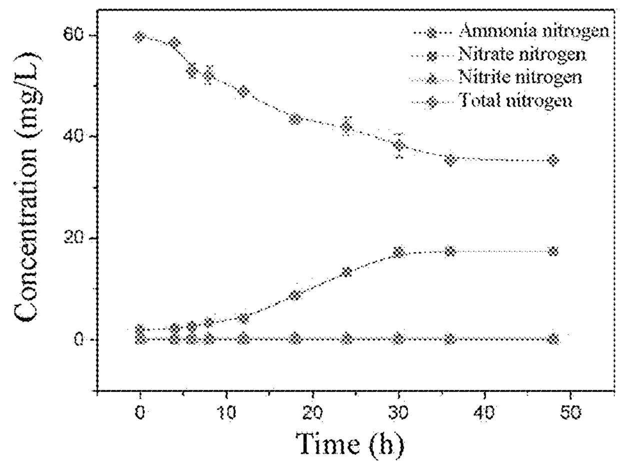
FIG. 2 shows removal effects of *Psychrobacter aquimaris* A4N01 on ammonia nitrogen, nitrite nitrogen and urea according to the present invention.

It should be noted that, the following detailed descriptions are all exemplary, and are intended to provide further descriptions of the present invention. Unless otherwise specified, all technical and scientific terms used herein have the same meanings as those usually understood by a person of ordinary skill in the art to which the present invention belongs.

It should be noted that the terms used herein are merely used for describing specific implementations, and are not intended to limit exemplary implementations of the present invention. As used herein, the singular form is also intended to include the plural form unless the context clearly dictates otherwise. In addition, it should be further understood that, terms "comprise" and/or "include" used in this specification indicate that there are features, steps, operations, devices, components, and/or combinations thereof.

As described above, salinity inhibits the nutrient bioconversion in high-salinity environments, resulting in great challenges in high-salinity wastewater treatment, difficulties in nutrients circulation in saline-alkali soil, which leads to a large amount of nutrients to be lost. The key for realizing nutrient conversion by the biological method is to find a salt-tolerant strain with the ability to utilize pollutants such as organic matters, nitrogen, and phosphorus, and to realize the stabilization of the functional strain in an environmental microbiome. Therefore, it is necessary to develop a method for developing halophilic microorganisms and microbiomes with clear metabolic pathways, rapid enrichment initiation and good comprehensive nutrient conversion ability in saline environments.

In view of this, in one implementation of the present invention, a strain of *Psychrobacter aquimaris* A4N01 is provided. The strain has been deposited in China Center for Type Culture Collection (address: Wuhan University, Luojiashan, Wuchang, Wuhan City, Hubei Province) on Jan. 20, 2021 with a biological deposit number of CCTCC NO: M 2021120. The strain can effectively metabolize ammonia nitrogen through nitrogen assimilation and has a self-flocculating ability. More importantly, during a metabolic process of the strain, no nitrate or nitrite is generated, nitrogen loss is avoided, and a salinity tolerance range is wide, so that integrated removal of nutrients such as carbon, nitrogen, and phosphorus can be realized.

Metabolites of the *Psychrobacter aquimaris* A4N01 also fall within the protection scope of the present invention.

In another implementation of the present invention, the metabolites of the *Psychrobacter aquimaris* A4N01 can be obtained from a fermentation broth of the *Psychrobacter aquimaris* A4N01. The metabolites of the *Psychrobacter aquimaris* A4N01 can be specifically prepared according to the following method: the *Psychrobacter aquimaris* A4N01 is inoculated into a liquid fermentation medium for fermentation culture, and the *Psychrobacter aquimaris A*4N01 in a liquid culture (the fermentation broth) is removed to obtain the metabolites of the *Psychrobacter aquimaris* A4N01.

The liquid fermentation medium is preferably a seawater LB medium.

Specific conditions for the fermentation culture are as follows: culture is performed at 20-30° C. (preferably 25° C.) for 20-30 h (preferably 24 h) with a rotating speed of 180-250 r/min (preferably 200 r/min).

Ingredients of the seawater LB medium are as follows:

10 g/L peptone, 3 g/L yeast extract, prepared with aged seawater with a seawater salinity of 3.3%.

In another implementation of the present invention, a microbial agent is provided, and the microbial agent contains the above *Psychrobacter aquimaris* A4N01 and/or the metabolites of the *Psychrobacter aquimaris* A4N01.

In another implementation of the present invention, in addition to the active ingredients, the microbial agent further contains a carrier. The carrier may be a carrier commonly used in the field of bacterial agents and being biologically inert.

The carrier may be a solid carrier or a liquid carrier.

The solid carrier may be a mineral material, a plant material or a polymer compound. The mineral material may be at least one of clay, talcum, kaolin, montmorillonite, white carbon, zeolite, silica and kieselguhr. The plant material may be at least one of corn flour, bean flour and starch. The polymer compound may be polyvinyl alcohol or/and polyglycol.

The liquid carrier may be an organic solvent, vegetable oil, mineral oil or water. The organic solvent may be decane or/and dodecane.

The microbial agent may be in variety dosage forms, such as liquid, emulsion, suspension, powder, granules, wettable powder or water dispersible granules.

As needed, the microbial agent may also be added with a surfactant (such as Tween 20, Tween 80, etc.), a binder, a stabilizer (such as an antioxidant), a pH regulator, etc.

In another implementation of the present invention, a halophilic nitrogen assimilation microbiome is provided, which contains the above *Psychrobacter aquimaris* A4N01 and/or the metabolites of the *Psychrobacter aquimaris* A4N01. More specifically, the halophilic nitrogen assimilation microbiome is obtained by inoculating the *Psychrobacter aquimaris* A4N01 into the high-salinity wastewater for culturing.

In another implementation of the present invention, the halophilic nitrogen assimilation microbiome may be the high-salinity wastewater obtained by the above treatment or activated sludge obtained by the above treatment.

In another implementation of the present invention, a method for constructing the above halophilic nitrogen assimilation microbiome is provided, which includes:

inoculating the above *Psychrobacter aquimaris* A4N01 into a bioreactor containing high-salinity wastewater, and operating until stable ammonia nitrogen removal efficiency and settling performance are realized, so as to obtain a halophilic nitrogen assimilation microbiome. According to the present invention, studies unexpectedly find that the *Psychrobacter aquimaris* A4N01 can promote the formation of the halophilic nitrogen assimilation microbiome. By managing a structure of the microbiome, a metabolic direction of the microbiome developed by the strain can be regulated without salinity gradient domestication. The method is rapid in initiation, short in time consumption, simple in operation and low in cost. Furthermore, the halophilic nitrogen assimilation microbiome also has good organic matter and phosphorus removal capacity and good settling performance, and can realize recycling of nutrients in the high-salinity wastewater. Meanwhile, the halophilic nitrogen assimilation microbiome contains a large amount of organic matters and organic nitrogen, so that can be used for organic fertilizer preparation, and has good practical application value.

Inoculated bacterial cells are controlled to be not less than 5 g/L.

The high-salinity wastewater may be actual high-salinity wastewater or may be simulated high-salinity wastewater. The simulated high-salinity wastewater has a salinity of not less than 2% (w/w) and is prepared with aged seawater.

More specifically, the simulated high-salinity wastewater includes the following ingredients: 0.8 g/L glucose, 0.5 g/L sodium acetate, 0.55 g/L ammonium chloride, 0.14 g/L dipotassium phosphate and 0.25 mg/L peptone, and the simulated high-salinity wastewater is prepared with the aged seawater with a salinity of 3.3%.

The bioreactor is a sequencing batch bioreactor (SBR). The sequencing batch reactor is an intermittent activated sludge system adopting one pool body. The pool body is used as both a bioreactor and a settling pool. When continuous flow of wastewater is treated, at least two or more pools are required.

The construction method is as follows:

Operation is carried out in a continuous mode. High-salinity wastewater with a salinity of 3-7% is used as influent. DO is controlled to be maintained at 2-3 mg/L through aeration. A carbon-nitrogen ratio of the influent is not less than 10. An operation cycle is 8 h, including 5 min of influent, 450 min of aeration, 15 min of settling and 10 min of effluent without mud discharging.

A volumetric exchange rate is 62.5%, and a hydraulic retention time (HRT) is 12.8 h.

In another implementation of the present invention, application of the above *Psychrobacter aquimaris* A4N01, the microbial agent and/or the halophilic nitrogen assimilation microbiome in any one or more of the following is provided:

a) single-cell protein synthesis;

b) recycling of nitrogen and phosphorus nutrients;

c) wastewater treatment;

d) preparation of organic fertilizer;

e) improvement of soil fertility;

f) saline-alkali soil bioremediation;

g) governance of eutrophic water body;

h) pollution restoration of water body; and i) greenhouse gas reduction and carbon neutral.

In b), nitrogen is metabolized based on assimilation.

In c), the wastewater includes high-salinity wastewater, aquaculture wastewater, industrial saline wastewater and seawater toilet-flushing wastewater.

In g), the water body includes freshwater and seawater, and seawater is preferred.

In another implementation of the present invention, a method for nutrient integration and resource conversion in a high-salinity environment is provided. The method includes applying the above *Psychrobacter aquimaris* A4N01, the microbial agent and/or the halophilic nitrogen assimilation microbiome to the high-salinity environment.

In another implementation of the present invention, the high-salinity environment is a high-salinity water environment, and the high-salinity water environment has a salinity of not less than 2% (w/w), further preferably of 3%-7% (w/w).

The following further explains and describes the present invention through embodiments, but does not constitute a limitation of the present invention. It should be understood that these embodiments are merely intended to describe the present invention rather than to limit the scope of the present invention.

Embodiment 1

A method for screening and culturing *Psychrobacter aquimaris* A4N01 included the following steps.

Marine sediments taken from the Yellow Sea (122°48'E, 35°59'N) were inoculated into a seawater LB medium, and subjected to shaking culture in a shaker under conditions of 25° C. and 200 r/min for 24 h. Supernatant was taken for streaking on a seawater LB solid plate.

Single colonies formed on the plate were respectively inoculated into the seawater LB medium, and subjected to shaking culture in the shaker under conditions of 25° C. and 200 r/min for 24 h. Microorganisms with a flocculation ability were screened out through observation.

The strains with the flocculation ability screened out above were inoculated in an ammonia nitrogen medium to investigate their ammonia nitrogen and total nitrogen removal capacities, and a strain with high ammonia nitrogen removal efficiency, no generation of nitrite and nitrate and no loss of total nitrogen in the system was screened, namely the *Psychrobacter aquimaris* A4N01 described in the present invention.

A measured 16 s rDNA sequence was input into a GenBank database website of an NCBI website for similarity comparison, and a phylogenetic tree was drawn. Results of the phylogenetic tree are shown in FIG. 1. The results show that the *Psychrobacter aquimaris* A4N01 has the highest similarity with *Psychrobacter aquimaris*, and in combination with physiology and biochemistry, colony morphology and indexes, the strain is identified and named as *Psychrobacter aquimaris* A4N01.

Embodiment 2

A method for determining physicochemical properties of nitrogen metabolism of the *Psychrobacter aquimaris* A4N01 was as follows.

(1) The *Psychrobacter aquimaris* A4N01 was inoculated into a seawater LB medium, and subjected to shaking culture in a shaker under conditions of 25° C. and 200 r/min for 24 h to prepare an activated bacteria solution. 1) The prepared *Psychrobacter aquimaris* A4N01 activated bacteria solution was centrifuged at 4,000 rpm for 10 min. 2) After supernatant was removed, bacterial cells were resuspended and washed with sterile normal saline (0.85% NaCl), and centrifuged at 4,000 rpm for 10 min. 3) After the bacterial cells were resuspended with the sterile normal saline, the bacterial cells were inoculated into mediums containing ammonia nitrogen, nitrite nitrogen and urea as a nitrogen source respectively at an inoculum size of 10%, and sampling was carried out at specified time points to determine the utilization and conversion of the strain on the various nitrogen sources.

In the above method, the ammonia nitrogen, nitrite nitrogen and urea mediums are prepared with aged seawater with a seawater salinity of 3.3%, and other ingredients are shown in Table 1.

TABLE 1

| Ingredient (mg/L) | Ammonia nitrogen medium | Nitrite nitrogen medium | Urea medium |
|---|---|---|---|
| Sodium acetate | 1,000 | 1,000 | 1,000 |
| $NH_4Cl$ | 230 | 0 | 0 |
| $NaNO_2$ | 0 | 295 | 0 |
| Urea | 0 | 0 | 130 |
| $KH_2PO_4$ | 400 | 400 | 400 |

It can be seen from FIG. 2 that the strain can use ammonia nitrogen, nitrite nitrogen and urea as the nitrogen source, and in an ammonia nitrogen conversion process, no nitrate or nitrite is generated. It can be seen from FIG. 3 that during the assimilation utilization of the ammonia nitrogen by the strain, total nitrogen in the system is converted from a water phase into biomass without nitrogen loss.

Embodiment 3

A method for determining physicochemical properties of nitrogen metabolism of the *Psychrobacter aquimaris* A4N01 was as follows.

The *Psychrobacter aquimaris* A4N01 was inoculated into a seawater LB medium, and subjected to shaking culture in a shaker under conditions of 25° C. and 200 r/min for 24 h to prepare an activated bacteria solution. 1) The prepared *Psychrobacter aquimaris* A4N01 activated bacteria solution was centrifuged at 4,000 rpm for 10 min. 2) After supernatant was removed, bacterial cells were resuspended and washed with sterile normal saline (0.85% NaCl), and centrifuged at 4,000 rpm for 10 min. 3) After the bacterial cells were resuspended with the sterile normal saline, the bacterial cells were inoculated into simulated wastewater with different salinities respectively at an inoculum size of 10%, and sampling was carried out at specified time points to determine the removal of ammonia nitrogen by the strain.

In the above method, the simulated wastewater with different salinities is prepared with 1%, 2%, 3%, 4% and 5% (w/w) sodium chloride, and other ingredients are shown in Table 2.

TABLE 2

| Ingredient | Concentration (mg/L) |
|---|---|
| Sodium acetate | 1,000 |
| $KH_2PO_4$ | 90 |
| $NH_4Cl$ | 200 |

Figure 4:
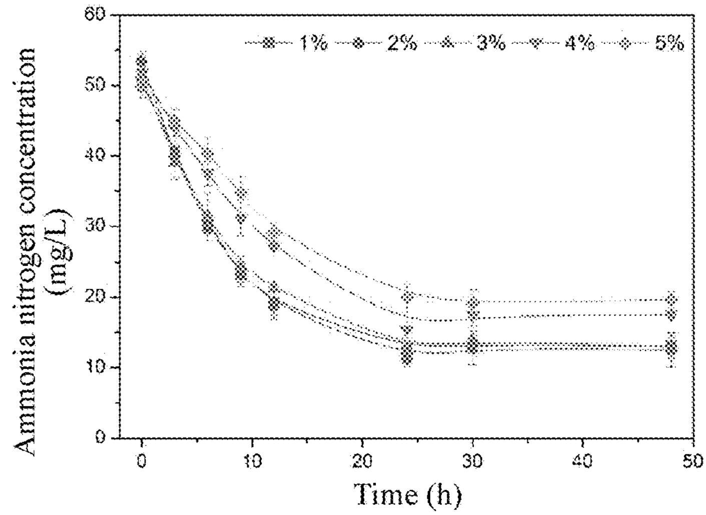
FIG. 4 shows removal of ammonia nitrogen by *Psychrobacter aquimaris* A4N01 under different salinity conditions according to the present invention.
Figure 5:
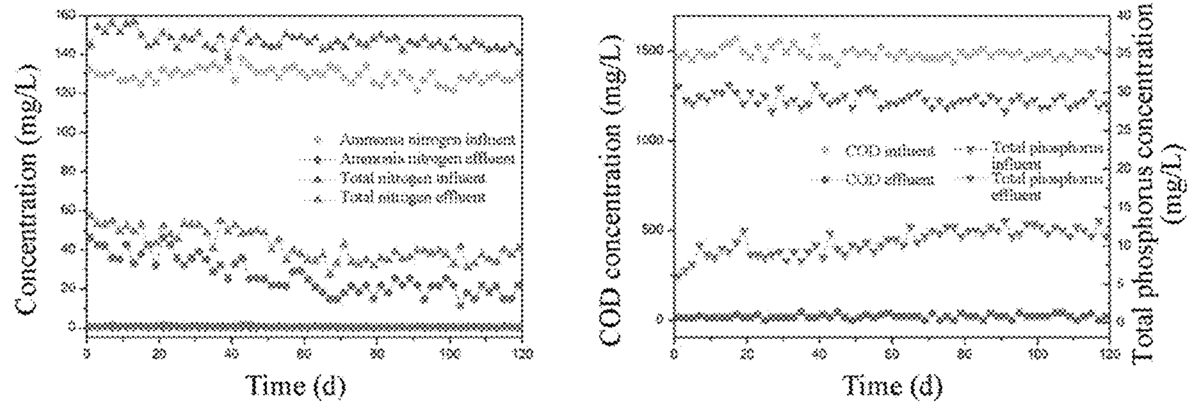
FIG. 5 shows removal of ammonia nitrogen, total nitrogen, COD and total phosphorus in a sequencing batch bioreactor according to the present invention.

It can be seen from FIG. 4 that the strain has a wide salinity tolerance range, and has a relatively high removal effect on the ammonia nitrogen under the salinity of 1-5%. In a salinity range of 1-3%, an ammonia nitrogen removal rate exceeds 74%, and in a salinity range of 4-5%, the ammonia nitrogen removal rate also exceeds 60%.

Embodiment 4

A method for developing a halophilic nitrogen assimilation microbiome by *Psychrobacter aquimaris* A4N01 included the following steps.

(1) The *Psychrobacter aquimaris* A4N01 was inoculated into a seawater LB medium, and subjected to shaking culture in a shaker under conditions of 25° C. and 200 r/min for 24 h to prepare an activated bacteria solution.

(2) The bacterial cells of *Psychrobacter aquimaris* A4N01 prepared in step (1) were inoculated into a sequencing batch bioreactor (SBR), and a concentration of the activated bacterial cells inoculated in the reactor was controlled to be about 5 g/L. An effective volume of the sequencing batch bioreactor (SBR) was 3.2 L. Operation was carried out in a continuous mode. An air diffusion device was mounted at a bottom for aeration and stirring. Each cycle of the reactor included four steps of influent, aeration, settling and effluent, including 5 min of influent, 450 min of aeration, 15 min of settling and 10 min of effluent. Each cycle was 8 h, a volume exchange rate was 62.5%, and a hydraulic retention time (HRT) was 12.8 h. During the operation, no mud was discharged. A halophilic nitrogen assimilation microbiome with stable ammonia nitrogen removal efficiency and good settling performance was obtained. Operating parameters of the sequencing batch bioreactor are shown in Table 3.

Ingredients of the seawater LB medium in step (1) are as follows:

10 g/L peptone, 3 g/L yeast extract, prepared with aged seawater with a seawater salinity of 3.3%.

TABLE 3

| Item | Parameter |
|---|---|
| Sludge retention time (d) | 21 |
| Hydraulic retention time (h) | 12.8 |
| Dissolved oxygen concentration (mg/L) | 2-3 |
| Temperature (° C.) | Room temperature |

When the sequencing batch bioreactor (SBR) was operating, synthetic wastewater was adopted to simulate ingredients of wastewater. The synthetic wastewater is prepared with aged seawater, and the ingredients thereof are shown in Table 4.

TABLE 4

| Ingredient | Concentration (mg/L) |
|---|---|
| Glucose | 800 |
| Sodium acetate | 500 |
| Peptone | 250 |
| $KH_2PO_4$ | 140 |
| $NH_4Cl$ | 550 |

Embodiment 5

Figure 3:
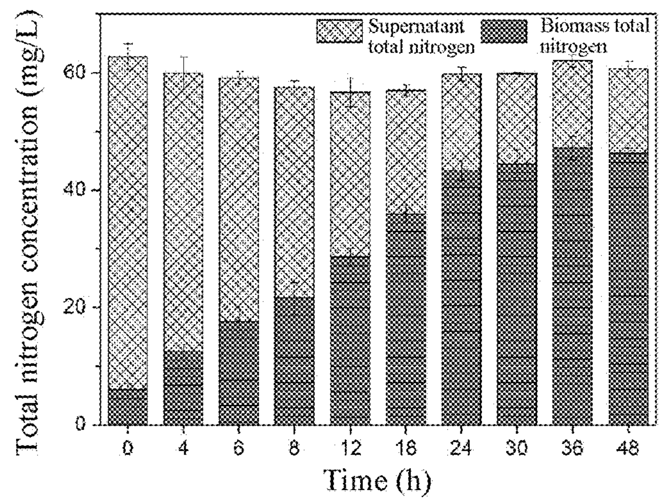
FIG. 3 shows total nitrogen balance when *Psychrobacter aquimaris* A4N01 uses ammonia nitrogen according to the present invention.

The halophilic nitrogen assimilation microbiome in Embodiment 4 was used to treat wastewater in a sequencing batch bioreactor (SBR) according to the condition of simulated high-salinity wastewater in Embodiment 4. Operating parameters of the reactor were the same as those in Embodiment 4. Sampling was carried out at specified time points to determine concentrations of COD, ammonia nitrogen, total nitrogen and total phosphorus of the wastewater. Operation results are shown in FIG. 3. It can be seen from the results that in the whole operation process, the halophilic nitrogen assimilation microbiome developed by the *Psychrobacter aquimaris* A4N01 has good and stable treatment effects. Final removal rates of ammonia nitrogen and total nitrogen in the simulated high-salinity wastewater can reach 84% and 75% respectively. The removal of nitrogen in the wastewater is mainly realized by assimilation without accumulation of nitrite and nitrate. Meanwhile, the halophilic nitrogen assimilation microbiome also has good removal capacity to organic matters and phosphorus in the simulated high-salinity wastewater. Final removal rates of COD and total phosphorus reach 98% and 72% or above respectively.

Embodiment 6

The halophilic nitrogen assimilation microbiome in Embodiment 4 was transferred into a batch medium according to an inoculum size of 5 g/L. A dissolved oxygen concentration was controlled to be 2-3 mg/L. Sampling was carried out at specified time points to determine ammonia nitrogen removal and conversion and total nitrogen balance within the operation cycle of 8 h.

The batch medium is prepared with aged seawater, and ingredients are shown in Table 5.

TABLE 5

| Ingredient | Concentration (mg/L) |
|---|---|
| Sodium acetate | 500 |
| $KH_2PO_4$ | 140 |
| $NH_4Cl$ | 550 |

Figure 6:
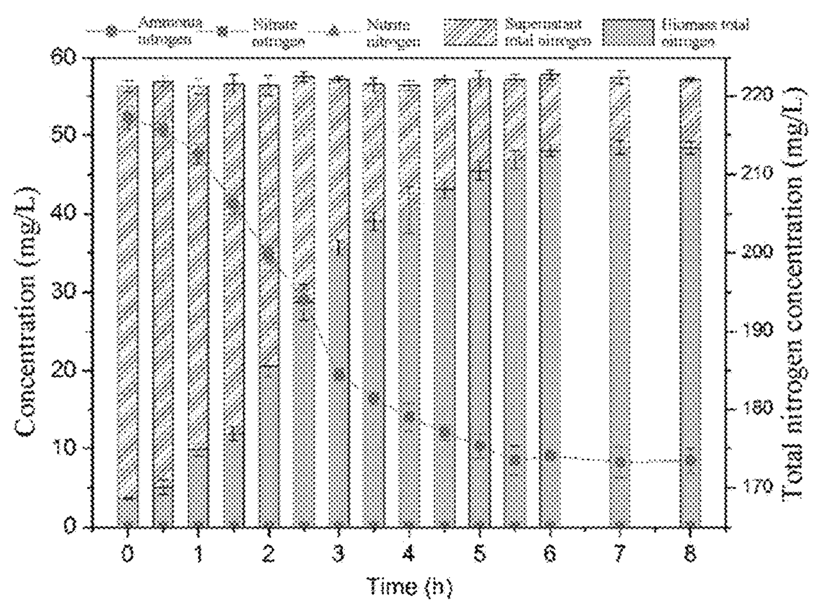
FIG. 6 shows nitrogen balance batch experiments of a halophilic nitrogen assimilation microbiome according to the present invention.

It can be seen from FIG. 6 that the microbiome developed by the *Psychrobacter aquimaris* A4N01 shows similar nitrogen utilization characteristics to the strain, and still removes ammonia nitrogen through nitrogen assimilation. In the process, no nitrite or nitrate is generated, and the removed ammonia nitrogen is accumulated into biomass without nitrogen loss.

Embodiment 7

Figure 7:
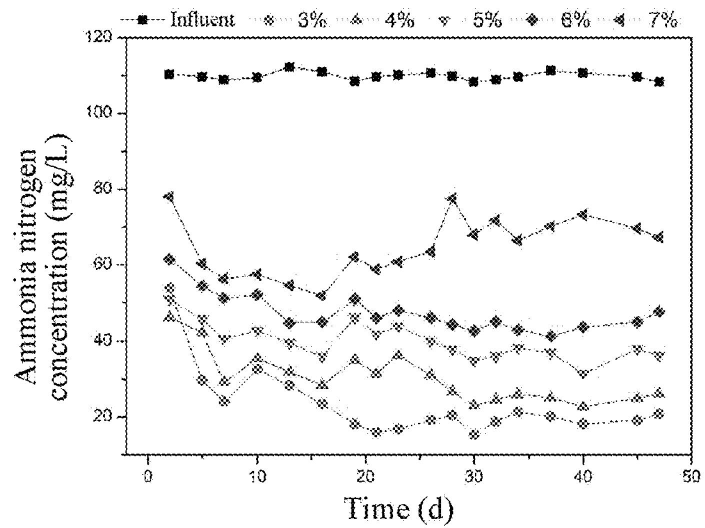
FIG. 7 shows operation of a halophilic nitrogen assimilation microbiome under different salinities according to the present invention.
Figure 8:
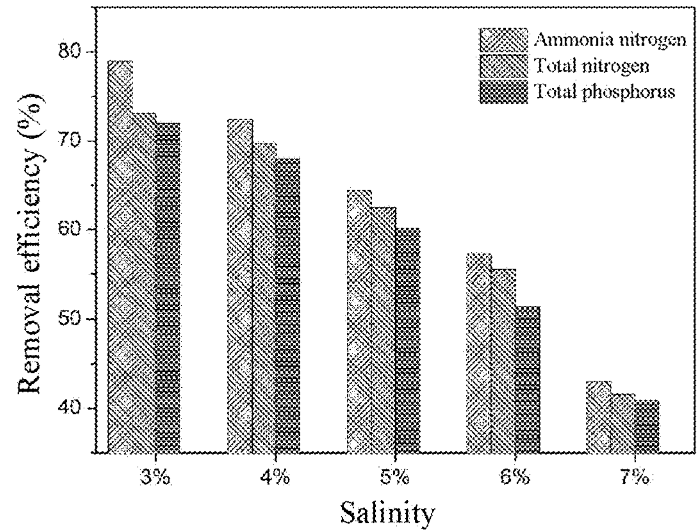
FIG. 8 shows ammonia nitrogen, total nitrogen and total phosphorus removal efficiencies of a halophilic nitrogen assimilation microbiome under different salinities according to the present invention.

Steps (1) to (3) were the same as those in Embodiment 4. Then the halophilic nitrogen assimilation microbiome was used to treat synthetic simulated high-salinity wastewater with a salinity of 3%, 4%, 5%, 6% and 7% (w/w) respectively in a sequencing batch bioreactor (SBR). Operating mode and parameters were the same as those in Embodiment 4. The simulated high-salinity wastewater had a carbon-nitrogen ratio of not less than 10, ammonia nitrogen of 100 mg/L and total phosphorus of 20 mg/L. A removal effect on the ammonia nitrogen in an operation process of nearly 60 d is shown in FIG. 7. It can be seen from the result that under different salinity conditions, a halophilic nitrogen assimilation microbiome treating system has a relatively short initiation time, and a stable operation effect. Average removal efficiencies of ammonia nitrogen, total nitrogen and total phosphorus are shown in FIG. 8. It can be seen from the result that the halophilic nitrogen assimilation microbiome obtained from Embodiment 4 has a relatively good salinity shock capacity. The halophilic nitrogen assimilation microbiome developed under a salinity of 3% (w/w) can be directly used for treating wastewater with a higher salinity without being subjected to salinity domestication. The halophilic nitrogen assimilation microbiome has strong adaptability. The halophilic nitrogen assimilation microbiome has a certain removal capacity to the ammonia nitrogen in the simulated high-salinity wastewater with a salinity of 3%-7% (w/w). When the salinity is not higher than 6%, the removal efficiency of the ammonia nitrogen in the simulated high-salinity wastewater is not lower than 50%. Furthermore, the removal of nitrogen in the wastewater is mainly realized by assimilation without accumulation of nitrite and nitrate as well as nitrogen loss. Meanwhile, the halophilic nitrogen assimilation microbiome also has a good removal capacity to phosphorus in the simulated high-salinity wastewater.

Embodiment 8

Steps (1) and (2) were the same as those in Embodiment 4. When a sequencing batch bioreactor (SBR) was operating, the operation was carried out according to the parameters in Table 3 in Embodiment 4, and sampling was carried out at specified time points to measure the ammonia nitrogen concentration.

In this embodiment, synthetic wastewater was adopted to simulate ingredients of wastewater. The synthetic wastewater is prepared with aged seawater, and ingredients are shown in Table 6.

TABLE 6

| Ingredient | Concentration (mg/L) |
| --- | --- |
| Sodium acetate | 1280 |
| $KH_2PO_4$ | 90 |
| $NH_4Cl$ | 200 |

Figure 9:
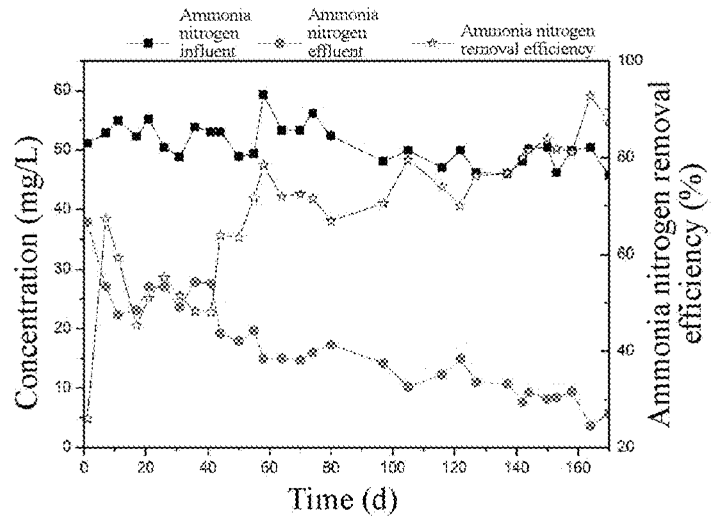
FIG. 9 shows a removal effect of a long-operating halophilic nitrogen assimilation microbiome on ammonia nitrogen according to the present invention.
Figure 10:
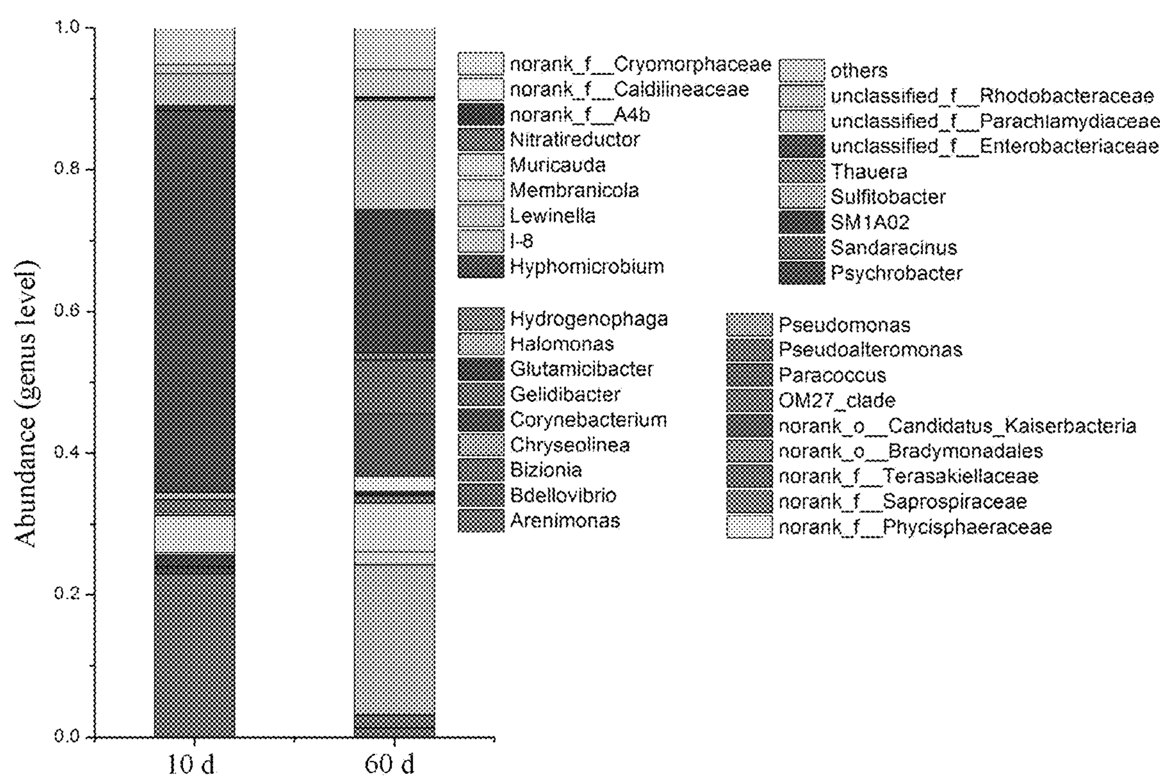
FIG. 10 shows a community structure composition of a halophilic nitrogen assimilation microbiome according to the present invention.

Operation results are shown in FIG. 9. It can be seen from the results that in an operation process of 170 d, the halophilic nitrogen assimilation microbiome has good and stable treatment performances. A removal rate of ammonia nitrogen in the simulated high-salinity wastewater is maintained to be 85% or above. Composition change of a community structure of the halophilic nitrogen assimilation microbiome is shown in FIG. 10.

In conclusion, the *Psychrobacter aquimaris* A4N01 has good salinity tolerance, and can efficiently recycle nitrogen, phosphorus and organic matters from high-salinity wastewater. Since a nitrogen metabolic process of the strain does not generate nitrate, nitrite and nitrogen loss, efficient recycling and conversion of nutrients in high-salinity wastewater can be realized, so that the strain can be applied to the fields such as high-salinity wastewater treatment and saline-alkali soil bioremediation in the future. The halophilic nitrogen assimilation microbiome developed by the *Psychrobacter aquimaris* A4N01 has relatively high contents of nitrogen, phosphorus and organic matters, so that the halophilic nitrogen assimilation microbiome is a good source of soil fertilizer. The strain can be prepared into fertilizer in the future, and applied to the fields such as soil improvement, and saline-alkali soil bioremediation.

It should be finally noted that the foregoing descriptions are merely preferred embodiments of the present invention, but are not intended to limit the present invention. Although the present invention has been described in detail with reference to the foregoing embodiments, for a person of ordinary skill in the art, modifications can be made to the technical solutions described in the foregoing embodiments, or equivalent replacements can be made to some technical features in the technical solutions. Any modification, equivalent replacement, or improvement made within the spirit and principle of the present invention shall fall within the protection scope of the present invention. The specific implementations of the present invention are described above, but are not intended to limit the protection scope of the present invention. A person skilled in the art should understand that various modifications or deformations may be made without creative efforts based on the technical solutions of the present invention, and such modifications or deformations shall fall within the protection scope of the present invention.

What is claimed is:

1. A method for constructing a halophilic nitrogen assimilation microbiome, the method comprising:

inoculating *Psychrobacter aquimaris* A4NO1 into a bioreactor containing high-salinity wastewater having a salinity of not less than 2% (w/w), and operating the bioreactor with operation cycles, each operation cycle comprising four steps of generating influent, aeration, settling and generating effluent to obtain a halophilic nitrogen assimilation microbiome, wherein the *Psychrobacter aquimaris* A4N01 has been deposited in China Center for Type Culture Collection on Jan. 20, 2021 with a biological deposit number of CCTCC NO: M 2021120.

2. The method according to claim 1, wherein the inoculated strain an inoculation amount of the *Psychrobacter aquimaris* A4N01 is controlled to be not less than 5 g/L; and the high-salinity wastewater is simulated high-salinity wastewater, the simulated high-salinity wastewater has a salinity of—not less than 2% (w/w) 3%-7% (w/w), and the simulated high-salinity wastewater is prepared with aged seawater.

3. The method according to claim 1, wherein the simulated high-salinity wastewater comprises the following ingredients: 0.8 g/L glucose, 0.5 g/L sodium acetate, 0.55 g/L ammonium chloride, 0.14 g/L dipotassium phosphate and 0.25 mg/L peptone, and the simulated high-salinity wastewater is prepared with aged seawater with a salinity of 3.3%.

4. The method according to claim 1, wherein:

the bioreactor is a sequencing batch bioreactor; and the sequencing batch bioreactor is operated in a continuous mode, high-salinity wastewater with a salinity of 3-7% is used as influent, DO is controlled to be maintained at 2-3 mg/L through aeration, and a carbon-nitrogen ratio of the influent is not less than 10.

5. The method according to claim 4, wherein an operation cycle of the sequencing batch bioreactor is 8 h, comprising 5 min of generating influent, 450 min of aeration, 15 min of settling and 10 min of generating effluent without mud discharging.

* * * * *